US011051761B2

(12) United States Patent
Courtney et al.

(10) Patent No.: US 11,051,761 B2
(45) Date of Patent: Jul. 6, 2021

(54) INTRAVASCULAR IMAGING CATHETERS AND METHODS OF USE THEREOF

(71) Applicant: SUNNYBROOK RESEARCH INSTITUTE, Toronto (CA)

(72) Inventors: Brian Courtney, Toronto (CA); Isaac Jourard, Toronto (CA); Deniz Jafari, Sharon (CA)

(73) Assignee: SUNNYBROOK RESEARCH INSTITUTE, Toronto (CA)

(*) Notice: Subject to any disclaimer, the term of this patent is extended or adjusted under 35 U.S.C. 154(b) by 865 days.

(21) Appl. No.: 15/183,576

(22) Filed: Jun. 15, 2016

(65) Prior Publication Data
US 2016/0361018 A1 Dec. 15, 2016

Related U.S. Application Data

(60) Provisional application No. 62/175,968, filed on Jun. 15, 2015, provisional application No. 62/187,047, filed on Jun. 30, 2015.

(51) Int. Cl.
A61B 5/00 (2006.01)
A61B 8/12 (2006.01)
(Continued)

(52) U.S. Cl.
CPC .......... A61B 5/6852 (2013.01); A61B 5/0084 (2013.01); A61B 8/12 (2013.01);
(Continued)

(58) Field of Classification Search
CPC .... A61M 2025/09125; A61M 25/0102; A61M 25/0032; A61M 25/0029; A61M 25/003; A61B 1/00105; A61B 1/00128
See application file for complete search history.

(56) References Cited

U.S. PATENT DOCUMENTS 5,485,845 A * 1/1996 Verdonk .................. A61B 8/12
600/463
5,707,354 A 1/1998 Salmon et al.
(Continued)

FOREIGN PATENT DOCUMENTS

EP 2823767 A1 1/2015
JP 05056977 3/1993
(Continued)

OTHER PUBLICATIONS

International Search Report, PCT/CA2016/050696, dated Oct. 14, 2016, 9 pages.
(Continued)

Primary Examiner — Katherine L Fernandez
Assistant Examiner — Colin T. Sakamoto
(74) Attorney, Agent, or Firm — Hill & Schumacher

(57) ABSTRACT

Intravascular imaging catheters are provided that include a distal sheath portion having a lumen that is configured to optionally receive a guidewire or an imaging assembly. The distal sheath portion may be configured to have dimensions such that when a guidewire is inserted through the lumen and extends through a distal exit port, the distal sheath portion may be employed as a microcatheter. External tissue may be imaged at a location at or near the distal end of the catheter, enabling, for example, the controlled imaging of a total occlusion, and the positioning of the distal end (and guidewire) within a true lumen associated with a total occlusion. A structural stop may be provided at or near the distal end of the distal sheath portion to prohibit extension of the imaging assembly out of the distal exit port, while permitting the extension of the guidewire through the distal exit port.

18 Claims, 8 Drawing Sheets

(51) Int. Cl.
*A61B 8/00* (2006.01)
*A61B 5/02* (2006.01)

(52) U.S. Cl.
CPC ............ *A61B 8/445* (2013.01); *A61B 5/0066* (2013.01); *A61B 5/02007* (2013.01); *A61B 5/6851* (2013.01)

(56) References Cited

U.S. PATENT DOCUMENTS

| | | | |
|---|---|---|---|
| 6,530,913 B1* | 3/2003 | Giba | A61B 18/24 604/523 |
| 6,572,553 B2 | 6/2003 | Crowley | |
| 7,245,959 B1 | 7/2007 | Wasicek | |
| 7,704,210 B2 | 4/2010 | Maschke | |
| 8,172,757 B2 | 5/2012 | Jaffe et al. | |
| 8,460,195 B2 | 6/2013 | Courtney et al. | |
| 8,712,506 B2 | 4/2014 | Courtney et al. | |
| 8,784,321 B2 | 7/2014 | Courtney et al. | |
| 2002/0166946 A1 | 11/2002 | Iizuka et al. | |
| 2007/0083100 A1 | 4/2007 | Schulz-Stubner | |
| 2008/0177139 A1* | 7/2008 | Courtney | A61B 5/0035 600/109 |
| 2008/0294037 A1 | 11/2008 | Richter | |
| 2009/0131798 A1 | 5/2009 | Minar et al. | |
| 2009/0264771 A1 | 10/2009 | Houben et al. | |
| 2013/0197432 A1* | 8/2013 | Von Oepen | A61M 25/003 604/96.01 |
| 2014/0180071 A1 | 6/2014 | Stigall | |
| 2014/0180127 A1 | 6/2014 | Meyer | |
| 2014/0180134 A1 | 6/2014 | Hoseit | |
| 2014/0236207 A1 | 8/2014 | Makower et al. | |
| 2014/0276028 A1 | 9/2014 | Stigall | |
| 2014/0358007 A1* | 12/2014 | Quistgaard | A61B 8/085 600/459 |
| 2015/0359433 A1 | 12/2015 | Stigall | |
| 2016/0331928 A1* | 11/2016 | Saphier | A61M 25/0023 |

FOREIGN PATENT DOCUMENTS

| | | | |
|---|---|---|---|
| JP | 910216 | 1/1997 | |
| WO | WO-2010036541 A1 * | 4/2010 | ............ A61M 25/00 |
| WO | 2015139031 A1 | 9/2015 | |

OTHER PUBLICATIONS

Written Opinion, PCT/CA2016/050696, dated Oct. 11, 2016, 9 pages.

* cited by examiner

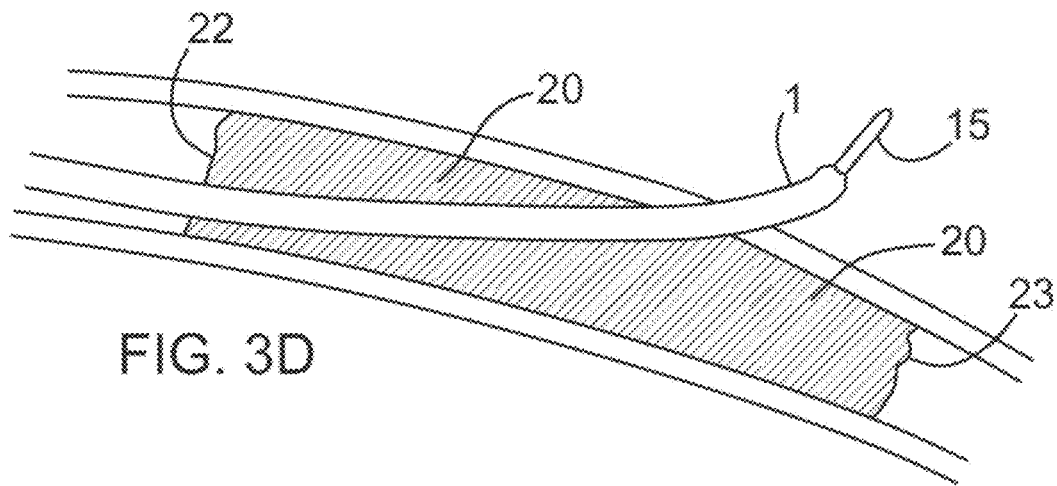
FIG. 3D
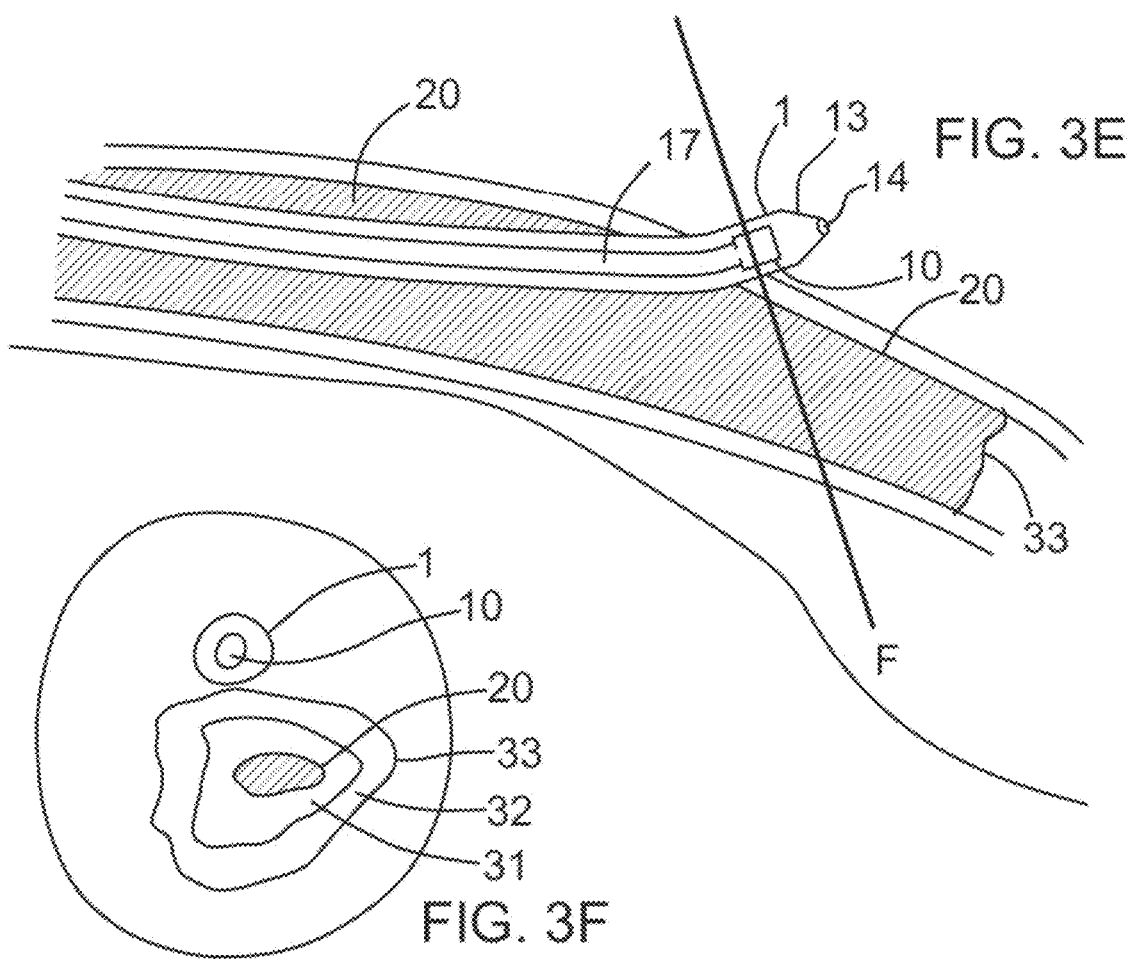
FIG. 3E
FIG. 3F

INTRAVASCULAR IMAGING CATHETERS AND METHODS OF USE THEREOF

CROSS-REFERENCE TO RELATED APPLICATION

This application claims priority to U.S. Provisional Application No. 62/175,968, titled "INTRAVASCULAR IMAGING CATHETERS AND METHODS OF USE THEREOF" and filed on Jun. 15, 2015, the entire contents of which is incorporated herein by reference, and to U.S. Provisional Application No. 62/187,047, titled "INTRAVASCULAR IMAGING CATHETERS AND METHODS OF USE THEREOF" and filed on Jun. 30, 2015, the entire contents of which is incorporated herein by reference.

BACKGROUND

The present disclosure relates to medical imaging. More particularly, the present disclosure relates to intravascular imaging in the presence of a total occlusion.

Intravascular imaging, such as intravascular ultrasound (IVUS) and optical coherence tomography (OCT), are frequently used for the assessment of coronary artery disease to supplement angiographic images. Most uses of intravascular imaging occur in vessels that are not occluded and therefore have some residual lumen through which angiographic dye, guidewires and imaging catheters can be delivered. Intravascular imaging is also occasionally used for interventions on total occlusions (such as chronic total occlusions). However, this typically occurs either after the total occlusion has been dilated open with an angioplasty balloon or after stent placement. In this context, the intravascular images provide an assessment of the results of the procedure.

Chronic total occlusions (CTOs) are particularly challenging lesions in which to perform interventional procedures, as they are difficult to visualize angiographically due to the absence of a lumen in which dye resides. The absence of a lumen also means that the routine techniques of advancing guidewires and other equipment that rely on a patent lumen surrounded by an arterial wall that confines the devices to remain intraluminal to direct the equipment are not as readily applied. They are also difficult to cross and often require the use of more aggressive and potentially traumatic devices, such as guidewires with stiff tips and devices that penetrate into the subintimal layers of the vessel and then re-emerge into the true lumen (also known as subintimal dissection and re-entry).

The use of IVUS or OCT to guide the treatment of CTOs is increasing and early data suggests it may improve procedural outcomes.

SUMMARY

Intravascular imaging catheters are provided that include a distal sheath portion having a lumen that is configured to optionally receive a guidewire or an imaging assembly. The distal sheath portion may be configured to have dimensions such that when a guidewire is inserted through the lumen and extends through a distal exit port, the distal sheath portion may be employed as a microcatheter. External tissue may be imaged at a location at or near the distal end of the catheter, enabling, for example, the controlled imaging of a total occlusion, and the positioning of the distal end of (and guidewire) within a true lumen associated with a total occlusion. A structural stop may be provided at or near the distal end of the distal sheath portion to prohibit extension of the imaging assembly out of the distal exit port, while permitting the extension of the guidewire through the distal exit port.

Accordingly, in a first aspect, there is provided an intravascular imaging catheter comprising:

a proximal elongate sheath comprising a first lumen;

an imaging conduit having a proximal portion housed within the first lumen and a distal portion extending beyond a distal end of said proximal elongate sheath;

an imaging assembly connected to said imaging conduit at a location that is remote from a proximal end thereof; and a distal elongate sheath comprising a second lumen, wherein the second lumen is in fluid communication with a distal opening formed at a distal end of said distal elongate sheath, wherein said distal elongate sheath is positionable within vasculature of a subject by extension of said distal elongate sheath over a guidewire when the guidewire is received within and extends through the second lumen beyond said distal end;

wherein the second lumen is configured to receive said distal portion of said imaging conduit therein upon withdrawal of the guidewire therefrom, such that said imaging assembly is extendable within the second lumen to a distal region of said distal elongate sheath, without extending beyond said distal end of said distal elongate sheath; and wherein a proximal end of said distal elongate sheath is removably connectable to a distal end of said proximal elongate sheath, such that when said distal portion of said imaging conduit is extended within the second lumen and said proximal elongate sheath is connected to said distal elongate sheath, the first lumen is in fluid communication with the second lumen, and said imaging conduit extends through the first lumen of said proximal elongate sheath and into the second lumen of said distal elongate sheath, and such that said imaging assembly resides within said distal region of said distal elongate sheath.

In another aspect, there is provided an intravascular imaging catheter comprising:

a first proximal elongate sheath segment comprising a first lumen;

a second proximal elongate sheath segment comprising a second lumen;

said first proximal elongate sheath segment and said second proximal elongate sheath segment joining to form a bifurcation region, such that the first lumen and the second lumen merge within said bifurcation region to form a third lumen; and a distal elongate sheath segment extending from said bifurcation region, wherein the third lumen extends within said distal elongate sheath segment and is in fluid communication with a distal opening formed at a distal end of said distal elongate sheath segment, wherein said distal elongate sheath segment is positionable within vasculature of a subject upon the extension a guidewire through the second lumen and the third lumen, such that the guidewire extends beyond said distal end of said distal elongate sheath segment;

an imaging conduit retractable within the first lumen; and an imaging assembly connected to said imaging conduit at a location that is remote from a proximal end thereof;

wherein said imaging conduit is extendable within the third lumen when the third lumen is absent of the guidewire, such that said imaging assembly is extendable within the third lumen to a distal region of said distal elongate sheath segment, without extending beyond said distal end of said distal elongate sheath segment.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 3A-F illustrate the use of the example intravascular imaging catheter within an occluded vessel.

DETAILED DESCRIPTION

Figure 1:
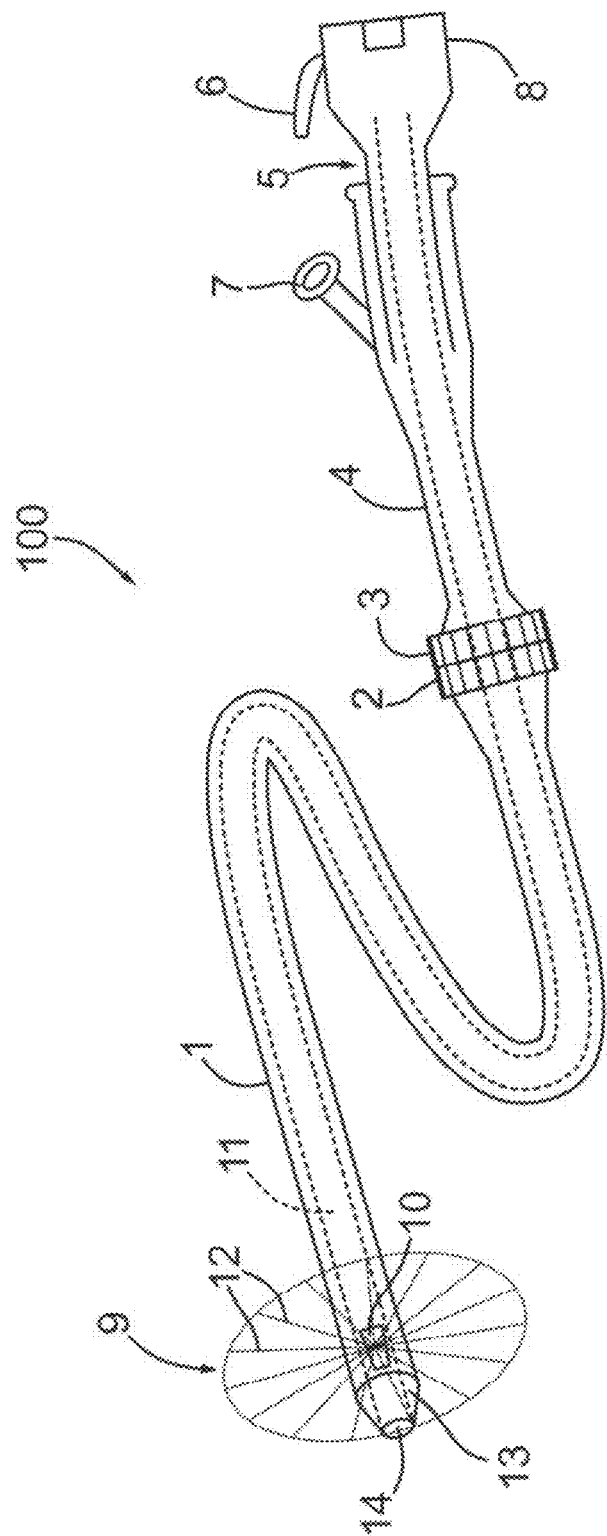
FIG. 1 shows an example of an intravascular imaging catheter having a distal sheath portion that is connected to a proximal sheath portion.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "includes" and "comprising" are to be construed as being inclusive and open ended, and not exclusive. Specifically, when used in the specification and claims, the terms "includes" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "microcatheter" refers to a catheter having a diameter, at least within a distal region thereof, that is less than 4 French (F) in diameter and typically less than or equal to 3 F in diameter. A microcatheter may have features that aid its deliverability through occlusions and into the distal vasculature, such as a tapered soft tip, wire braided reinforcement of the wall over all or a portion of its length, a hydrophilic coating on its outer surface and a lubricious lining (such as a PTFE liner) on the inner surface of the wall. There may also be a marker band, such as a gold, platinum or other radio-opaque material marker band in the distal tip to help it be readily identifiable on fluoroscopy. A microcatheter may have a single lumen or a plurality of lumens.

One of the limitations of most IVUS and OCT catheters is that they are side-viewing in nature, and collect images by rotating an ultrasound beam or optical beam around the long axis of the catheter. Usually, the beam has an angle of 80 to 90 degrees relative to the longitudinal axis of the catheter, allowing the creation of cross-sectional images. In some embodiments disclosed in the art (Novelis, others) the beam is tilted in a more forward viewing direction.

Intravascular imaging catheters typically have a guidewire lumen near the distal end in what is referred to as a rapid-exchange configuration. In this configuration, the distal portion of the catheter (say 5 to 20 mm) is configured to surround a guidewire that exits the guidewire lumen at the distal end of the catheter via a distal guidewire port. A more proximal portion of the guidewire exits the catheter's guidewire lumen via a proximal guidewire port that is typically 5 to 20 mm proximal to the distal guidewire port.

Due to the limited diameter of the intravascular imaging catheter (constrained by the size limitations imposed by the diameter of vessels such as coronary arteries), the imaging assembly from which the ultrasound or imaging beam radiates from the catheter is typically offset proximal to the proximal guidewire port. Thus, the distance between the tip of an intravascular imaging catheter and the region imaged by the intravascular imaging catheter is typically greater than the length of the guidewire lumen.

In many cases in intravascular imaging, it is desirable to have as short as possible of a distance between the tip of the intravascular imaging catheter and the region from within the catheter at which the imaging beam exits the catheter. However, with a conventional intravascular imaging catheter, the technique used is to first advance a guidewire far enough into the vasculature such that an intravascular imaging probe can then be advanced over the guidewire to get to the target space. The guidewire preferably should always extend beyond the distal tip of the intravascular imaging catheter to minimize the likelihood of trauma to the anatomy from the distal tip of the intravascular imaging catheter. This means that, at a minimum, with conventional intravascular imaging catheters, the closest that an imaging transducer could get to a blunt occlusion in the cardiovascular anatomy without having the guidewire penetrate into the occlusion is the sum of i) a short length of guidewire extending out past the distal tip of the intravascular imaging catheter, and ii) the distance between the distal tip of the intravascular imaging catheter and the imaging assembly within the intravascular imaging catheter.

The problem posed by this limitation is further exacerbated by the fact that most intravascular imaging catheters are delivered over guidewires that have a stiff long portion, followed by a more floppy tip. The floppy tip of the guidewire is intended to increase deliverability of the guidewire through non-occluded vessels while minimizing trauma during its delivery. The floppy tip is conventionally 35 to 45 mm long, but other lengths are available and there is a great deal of variability in guidewire design. If the distal tip of the intravascular imaging catheter is advanced onto the floppy tip of the guidewire, it is more likely that upon retraction (withdrawal) of the intravascular imaging catheter over the guidewire, that the floppy tip of the guidewire will buckle, thus damaging the guidewire, the intravascular imaging catheter and/or the anatomy through which the surrounding anatomy. The ability to advance intravascular image catheters in distal vasculature, in small vessels and near occlusions is limited in part by the ability to bring the imaging portion of the intravascular imaging catheter into a position near an anatomic region of interest during the procedure such that the desired views can be obtained.

Furthermore, it is desirable to have configurations of intravascular imaging catheters with as low a profile as possible to minimize trauma during insertion of the imaging catheter (such as if the catheter unintentionally exits the lumen of the artery and puts the patient at risk for a coronary perforation) and to minimize compression of the true lumen such that it is more easily recognizable by intravascular imaging.

Terumo has introduced an IVUS catheter that has a very short distance between the tip of the IVUS catheter and the ultrasound transducer, called the Navifocus WR. Its design minimizes the distance between the transducer and the catheter tip, but does not address the fact that a significant length of guidewire needs to be advanced ahead of the catheter. However, the monorail guidewire lumen runs parallel to the imaging lumen over most of its distal length and thus the maximum cross-sectional dimension for the distal portion of this catheter is larger (2.4 F or 0.8 mm for the imaging lumen and another approximately 1.5 F or 0.5 mm for the guidewire lumen, leading to a total maximum dimension of approximately 1.3 mm).

Referring back to how a chronic total occlusion is treated, it will become apparent that the distance between the tip of the imaging catheter and the points at which imaging energy exits the imaging catheter (and thus generates images) is a limitation of the utility of intravascular imaging during CTO revascularization procedures.

Typically, the CTO is crossed using one or more guidewires. Softer guidewires are less traumatic, but may not be strong enough to penetrate through fibrous cap or calcified regions in coronary occlusions. Stiffer wires have more directional control and pushability, but may cause more trauma to the vessel and surrounding anatomy, such as by causing dissections or perforations to the vessel.

Causing trauma with a wire such as a dissection or perforation can have variable consequences, depending on the location of the trauma and the physiologic significance of the trauma. For example, advancing a wire in the subintima of a vessel that is completely occluded is less likely to cause a physiologically meaningful dissection flap or ischemia, as the vessel is already occluded and therefore the layers of the vessel wall push against each other with little neighboring blood flow. Therefore the creation of a dissection in a CTO is unlikely to abruptly deprive a significant region of myocardium of blood. In fact, many CTO operators advance devices such as angioplasty balloons, blunt dissection devices and re-entry devices into the subintimal space of a CTO to work towards creating a new lumen across the length of the CTO. However, it is highly desirable to create that new lumen within the adventitial boundaries of the occluded vessel to ensure that there is some structural support for the new lumen that might otherwise result in loss of the gross architecture of the new lumen and potentially result in a perforation. Perforation of a coronary vessel into the pericardial space can result in fluid accumulating into the pericardial space causing a condition called tamponade, which is potentially acutely life threatening.

Extending a dissection plane significantly beyond the distal cap of a CTO can also have clinical consequences, as the distal vasculature may be fed by collateral branches and involved in the perfusion of functioning myocardium. Creating a dissection in the distal vascular can compromise the perfusion and thus potentially cause ischemia or infarction.

It should be mentioned that while perforation with a small wire can be dangerous in some situations, it is the advancement, dilatation and deployment of balloons and stents over a guidewire that can introduce the most risk during a CTO procedure if the guidewire does not reside within the true lumen of the occluded vessel, where a perforation or dissection can be expanded in size, thus increasing the severity of a perforation or the extent of a region effected by a dissection. The advancement of a wire into a false lumen or into the pericardial space is much more likely to be a recoverable situation if balloon dilatation has not yet taken place.

In some situations where intravascular imaging is used to facilitate CTO procedures, the imaging catheter may be placed in an adjacent vessel or in a branch of the same vessel to help with guiding the penetration of the fibrous cap of a CTO. IVUS is perhaps more useful for this as, unlike most optical methods, IVUS can see through blood and provide real-time imaging without the need to transiently displace blood from the field of view. This act of penetrating the fibrous cap or entry point into the CTO is a frequently challenging step that may require the use of a stiff guidewire and is frustrated in many cases by the absence of angiographic clues that help the operator identify the entry point into the CTO. Intravascular imaging can help identify the entry point and provide visual guidance/confirmation during the advancement of the wire if the imaging portion of the catheter can be advanced into a position and orientation close enough to the entry point that places the proximal portion of the cap into the field of view of the imaging catheter.

Another situation in which an imaging catheter can be useful during a CTO procedure is to confirm that the wire resides within at least the adventitial contour of the vessel, and preferably in the true lumen of the vessel. Advancing an intravascular imaging catheter over the guidewire and into the CTO may cause some trauma to the vessel, but is generally less traumatic than deploying a balloon or stent in the wrong location. If the adventitial and/or intimal layers of the vessel can be identified as surrounding the intravascular imaging catheter, this generally provides some reassurance that the guidewire is within the confines of the vessel over at least the portions of the CTO that can be imaged with the intravascular imaging catheter.

Alternatively, if the intravascular imaging catheter (and thus the guidewire over which it was delivered) is found to have exited the true lumen or the adventitial contours, one or more additional guidewires might be advanced into the CTO to try and create a preferred path through the CTO. It may then be possible to visualize the position of additional guidewires during their manipulation by the operator while the intravascular imaging catheter is in place and thus be possible to achieve a preferred path through the CTO more easily. It should be mentioned that once the imaging portion of an intravascular imaging catheter has exited a patent lumen and has entered into a CTO, there is far less blood in the field of view and it may be easier to use optical imaging within the CTO as compared to in a lumen where there is blood.

Another situation in which an intravascular imaging catheter is potentially useful for CTO procedures is in confirming whether or not the guidewire has successfully entered into the true lumen of the distal vasculature. It is occasionally difficult to confirm angiographically whether or not guidewire has advanced through the lesion and exited into the true lumen of the distal vasculature. It is preferable to ensure that the wire (and subsequently the balloons and stents) are in the true lumen rather than within the layers of the wall, as continuing along in such a procedure without having confidence that the distal end of the wire is in the true lumen can greatly complicate the procedure.

In CTO interventions, the use of microcatheters in combination with guidewires is common. Microcatheters are typically thin catheters with one or more lumens large enough to accommodate a guidewire. Many microcatheters are 1.8 F in diameter and can accommodate a 0.014" coronary guidewire, but other sizes are available to accommodate coronary and peripheral interventions. Examples of microcatheters in use include the FineCross catheter, the Supercross, the Corsair, the Valet Microcatheter and others. The use of a microcatheters may enhance the torquability and deliverability of a guidewire through portions of the coronary anatomy that are calcified, tortuous or severely stenotic/occluded by providing a better interface with the surface of the wire. Furthermore, microcatheters play an important role in terms of facilitating the use of different guidewire configurations at different times during an attempt to traverse an occlusion. For example, it may be desirable to advance a particular guidewire with a preferred bend to the entry point of a CTO. For example, this may be a soft tip wire (such as a BMW or Whisper wire) with a modest bend at the tip to help navigate the proximal portion of the coronary vasculature.

Once the guidewire is at the entry point, it may be preferable to use a guidewire that has a much stiffer tip, such as a Confianza wire or Miracle Bros wire with a very short bend at the tip. In order to switch from one wire type to another, a microcatheter can be advanced over the first wire. The first wire can then be withdrawn from the vasculature through the microcatheter. Then, the next wire can be advanced through the microcatheter. This technique helps provide a reliable and less traumatic path for the second wire to get to approximately the same position as where the first wire was previously advanced. The microcatheter may have a relatively atraumatic tip, depending on its design. Then, once the second wire is advanced through the proximal entry point of the CTO, the second wire can be advanced some distance through the CTO.

At some point (either within the CTO, upon approach to the distal exit point or even upon reaching the distal vasculature), it may be desirable to then exchange the second wire out for yet another wire, such as a wire with a less traumatic tip, a wire specifically designed to carry a rotational atherectomy device or some other wire. The microcatheter can be advanced at any time over the wire to either help facilitate delivery of the wire or to enable the exchange of one wire for another. Once a guidewire has successfully reached the distal vasculature, the use of balloons, stents and other interventional devices to revascularize the CTO can be used to get the desired result of revascularizing the CTO.

At any point during the performance of a CTO procedure or other interventional procedures, it may be desirable to perform imaging from within a microcatheter, and in particular, near the distal tip of a microcatheter.

A first example embodiment of the disclosure is provided in FIG. 1. An example intravascular imaging catheter 100 includes a separable outer sheath with a distal elongate sheath portion 1 and a proximal elongate sheath portion 4, where the proximal 4 and distal sheath portions 1 of the separable outer sheath are removably connectable via distal sheath connector 2 and proximal sheath connector 3. In one example implementation, connectors 2 and 3 may be mating Luer connectors, as is commonly used in interventional catheters, or, for example, magnetic connectors, snap connectors, screw-threaded connectors or other connectors that provide a mechanical connection and preferably a water-tight connection.

The proximal sheath portion 4 may further include a connector 8 that connects the intravascular imaging catheter to a patient interface module (alternatively called a motor drive unit). In one example implementation, connector 8 may include a latch or release button 6 that latches the proximal connector 8 to a motor drive unit.

The outer sheath contains a main lumen 11, formed by a first lumen that extends through the proximal sheath portion 4 and a second lumen that extends through the distal sheath portion 1. The first and second lumens are brought into fluid communication when the two sheath portions are connected.

As described below, the main lumen 11 has a diameter suitable for the insertion of an imaging assembly 10 via a longitudinal shaft or cable (e.g. a torque cable for rotating the imaging assembly within the distal sheath portion 1), henceforth referred to as an imaging conduit. The imaging assembly is connected to the imaging conduit at a location that is remote from a proximal end of the imaging conduit.

For example, FIG. 1 shows imaging assembly 10 located near a distal end of distal sheath portion 1, where imaging assembly 10 is rotatable within main lumen 11, for example, via rotation of the imaging conduit (not shown in FIG. 1) that extends within main lumen 11 from the proximal connector 6 into the distal sheath portion 1. During rotation, imaging beams 12 can be transmitted into, and received from, the local external environment in order to obtain signals for generating an image within the field of view 9. In one example embodiment, the imaging beams 12 may be ultrasound beams. In another example embodiment, the imaging beams 12 may be optical beams. The imaging beams 12 may corresponding to a single imaging modality, or a plurality of imaging modalities.

As shown in FIG. 1, a flush port 7 may optionally be attached to or integrated with the proximal sheath portion 4 (or some other portion of the proximal portion of the catheter), where the flush port 7 provides a port through which fluid can be introduced into the main lumen 11, for example, in order to flush the catheter of air.

As shown in FIG. 1, the proximal sheath portion 4 may also have two separate sheath components (4 and 5) that slide longitudinally with respect to each other to enable longitudinal translation (e.g. pullback) of the imaging assembly 10 within the intravascular imaging catheter 100.

As shown in FIG. 1, the main lumen 11 of the intravascular imaging catheter is sufficiently large enough to accommodate the insertion and internal translation (and optional rotation) of the imaging assembly 10 and an associated imaging conduit (such as a torque cable and either some electrical conductors or one or more fiber optics). As will be described in further detail below, in some embodiments, a distal region of main lumen 11, within the distal sheath portion 1, may be sufficiently narrow to prohibit the imaging assembly from extending beyond the distal end of the distal sheath portion 1.

The second lumen of the distal sheath portion is also sufficiently large to accommodate a guidewire in the absence of the insertion of the imaging assembly 10 and the imaging conduit. As will be known to those skilled in the art, guidewires range in size, however, in coronary interventions, guidewires are typically approximately 0.014" in diameter, and typically range from 0.009" to 0.018" in diameter, with guidewires typically being 0.014" to 0.038" for peripheral interventions.

The distal sheath portion 1 is long enough to extend through a guide catheter (not shown) and into the vasculature, where the guide catheter is separate from catheter 13, such that catheter 13 can be inserted into the guide catheter. For coronary applications, guide catheters are typically 90 to 100 cm long. As such, in coronary applications, the distal sheath portion of catheter 13 is typically more than 90 cm long and more typically 120-160 cm long, such that its distal end can be extended beyond the distal end of the guide catheter.

Figure 2A:
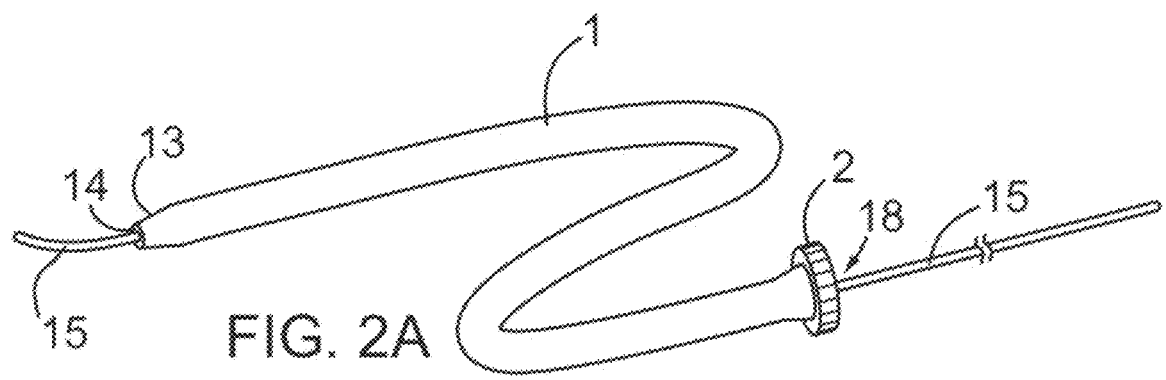
FIGS. 2A-B show the example intravascular imaging catheter in its disconnected state, showing the distal sheath portion (FIG. 2A) and the proximal sheath portion (FIG. 2B).
Figure 2B:
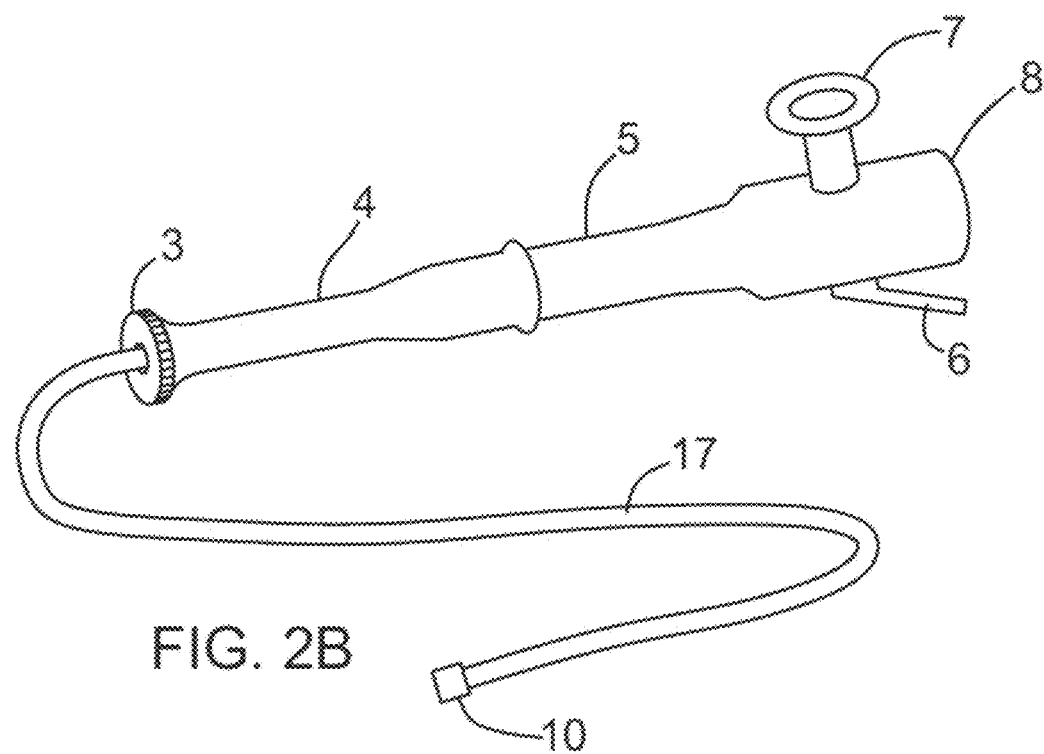

FIGS. 2A and 2B show the example intravascular imaging catheter with the proximal sheath portion 4 separated from distal sheath portion 1, where FIG. 2A shows the distal sheath portion housing a guidewire, and FIG. 2B shows the proximal sheath portion having the imaging shaft/conduit extending therefrom.

As shown in FIG. 2A, distal sheath portion 1 may be configured with dimensions such that when it is separated from the proximal sheath portion 1, it can be used as a microcatheter upon insertion of a guidewire 15 within main lumen 11. In such embodiments, distal sheath portion 1 may be referred to as a microcatheter portion. As shown in FIG. 2A, a distal opening (exit port) 14 is provided at the distal end of the distal sheath portion 1, thereby allowing a guidewire 15 to exit the distal sheath portion 1 (or for the insertion of a guidewire into the distal sheath portion 1). The guidewire 15 can be any suitable length of guidewire, and is typically 150 to 300 cm long, with 190 cm as a common length. Proximally, the guidewire 15 can exit or enter the lumen the outer sheath 1 via a proximal port 18 of the main lumen in outer sheath 1. Accordingly, the distal sheath portion may be positioned within vasculature of a subject by extension of the distal sheath portion over a guidewire when the guidewire is received within and extends through the second lumen of the distal sheath.

The outer diameter of the insertable portion of the catheter 13 is typically 1.8 F-4 F (0.6-1.33 mm) in diameter and the outer diameter may vary over the length of the catheter from a smaller diameter distally to a larger diameter proximally, thus providing improved deliverability of the catheter over the guidewire. In one example implementation, the distal-most portion of the distal sheath portion may taper down to the smallest dimension of the inner lumen 11.

Referring now to FIG. 2B, a portion of the imaging conduit 17 is shown as being housed and supported within the proximal sheath portion 4. The detachment of the distal sheath portion 1 and the proximal sheath portion 4 from each other allows withdrawal of the imaging conduit 17 and imaging assembly 10 from distal sheath portion 1.

As described above, when the two sheath portions are disconnected, such that the imaging conduit 17 does not reside with the second lumen of the distal sheath portion 1, a guidewire 15 may be inserted thought the distal sheath portion 1. Upon withdrawal of the guidewire 15, the distal portion of the imaging conduit 17 and the imaging assembly 10 may be extended within the second lumen, such that the imaging assembly 10 resides at or near a distal region of the distal elongate sheath. As described in further detail below, the distal region of the distal sheath portion may be configured to prohibit the extension of the imaging assembly 10 beyond the distal end of the distal elongate sheath.

In the example embodiment shown in FIGS. 1 and 2A-B, imaging conduit 17 and imaging assembly 10 are rotatable within the proximal sheath portion 1 and in the distal sheath portion (in the later case, when the distal sheath portion 4 is connected to the proximal sheath portion 1). Proximal connector 8 may contain a rotating insert (not shown) that is directly connected to the imaging conduit 17 such that the rotating insert, the imaging conduit 17 and the imaging assembly 10 rotate in unison within the housing of proximal connector 8, optional sheath extension 5 (that optionally enables pullback, as noted above) and proximal sheath portion 4 and in distal sheath portion 1 when it is attached to the proximal sheath portion 4. The proximal connector thus provides a mechanism or means to couple mechanical rotational motion from a patient interface module (also known as a motor drive unit) to the rotating components of the intravascular imaging catheter 100. Furthermore, the proximal connector 8 provides appropriate electrical and/or optical connectors to either (or both) the rotating and non-rotating components of the intravascular imaging catheter.

FIGS. 3A through 3F illustrate various example and non-limiting uses of imaging catheters configured according to embodiments of the present disclosure. In these example illustrations, the distal sheath portion 1 is configured as a microcatheter, and thus is referred to as a microcatheter portion 1. As shown in FIGS. 3A-F, a vessel 25 contains a total occlusion 20 with a proximal cap 22 and a distal exit point 23, with distal vasculature 21 that is perfused via a collateral vessel 24.

Figure 3A:
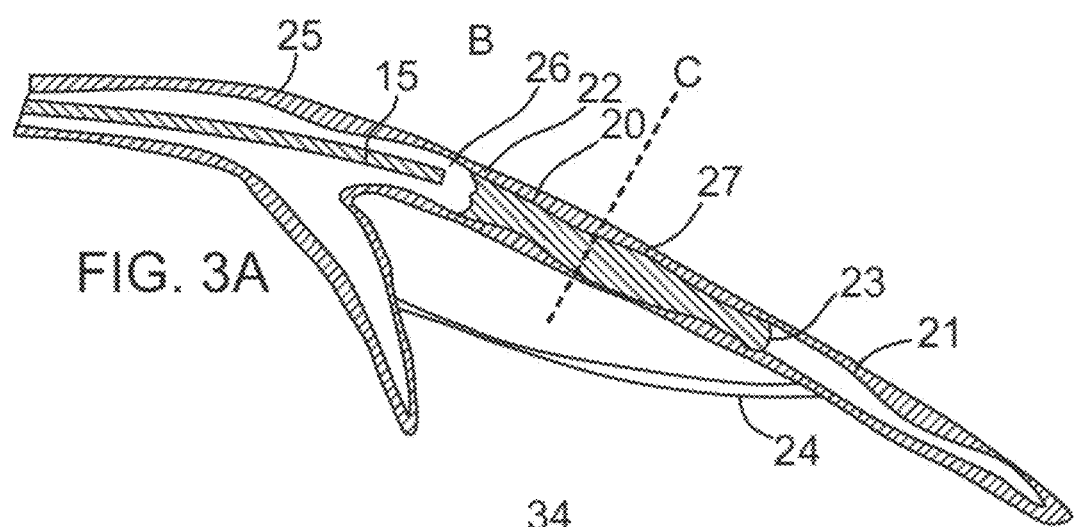
Figure 3B:
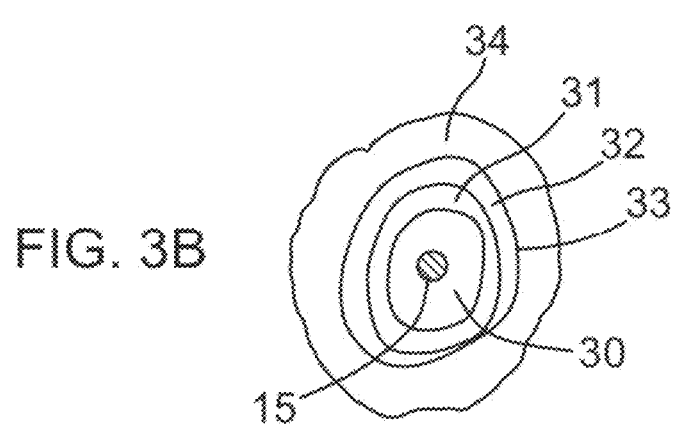

Referring now to FIG. 3A, a guidewire 15 can be advanced into the stump 26 of the vessel 25 that lies immediately proximal to proximal cap 22. This advancement of the guidewire 15 can be performed, for example, with the guidewire either within the microcatheter portion 1 of the intravascular imaging catheter (interchangeable with distal sheath portion 1) or without (the microcatheter portion 1 is not shown in FIG. 3A). If the microcatheter portion 1 is initially used in combination with a soft, atraumatic guidewire and a stiffer tip wire is desired, the microcatheter portion 1 can be used to exchange guidewires such that the stiffer tip guidewire is safely introduced into stump 26.

Figure 3C:
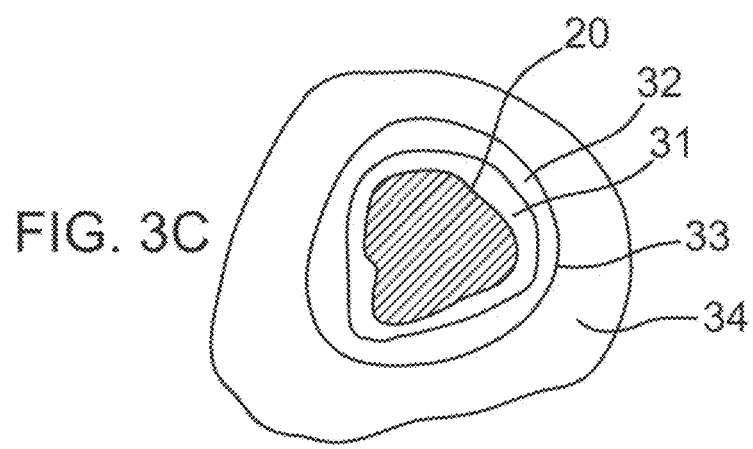

It is noted that the wall 27 of the vessel 25 shown in FIG. 3A has a finite thickness. The wall 27 is composed of several layers. In the cross-section B shown in FIG. 3B, the wall 27 has a patent lumen 30 (in which the guidewire resides), an intima layer 31, one or more media layers 32 and an adventia 33, surrounded by peri-adventitial tissue (such as fat, myocardium or potentially pericardium). In contrast, cross-section C shown in FIG. 3C shows the presence of a total occlusion 20.

As shown in FIG. 3D, a guidewire 15 can then be advanced into the occlusion 20 through the proximal cap 22. The guidewire 15 would preferably remain within the true lumen of the occlusion, or at least within the adventitial boundary, but may also perforate out of the artery (as shown in FIG. 3D). Microcatheter portion 1 could be advanced over the wire, also as shown in FIG. 3D. The wire could then be removed, leaving the microcatheter portion 1 in place.

As shown in FIG. 3E, the imaging assembly 10 and imaging conduit 17 could be advanced into the microcatheter portion 1 once the proximal sheath portion 4 and distal sheath portion 1 are connected to each other. Optionally, the imaging assembly 10 can then be advanced as distally as possible in the lumen 11 of the microcatheter portion 1 by advancing sheath section 5 of the proximal sheath portion into sheath section 4 of the proximal portion (sheath sections 4 and 5 are shown in FIGS. 1 and 2B).

Having located the imaging assembly within the distal region of the microcatheter portion 1, imaging can then be initiated. In the case of using a side-viewing imaging assembly (as shown in the example embodiment illustrated in FIG. 1), a cross-section image can be taken through section F, which is represented in FIG. 3F. As shown in FIG. 3F for this example, the imaging assembly 10 and a distal region of the microcatheter portion 1 are outside of the adventitia 33 of the occlusion. The imaging assembly 10 can then be pulled back within the lumen 11 of the microcatheter portion 1, such as by sliding sheath sections 4 and 5 of the proximal sheath portion 4 apart along each other (withdrawing sheath section 5 from sheath section 4).

When the imaging assembly 10 passes through line G, it will be apparent as to where the imaging assembly 10 and surrounding cross-section of the microcatheter portion 1 are within the true lumen of the CTO. The microcatheter portion 1 can be then retracted (e.g. by retracting the microcatheter portion 1 by a longitudinal distance equal to, or approximately equal to, the pullback distance). Alternatively, another guidewire can be introduced into occlusion 20, for example, under both fluoroscopic guidance and guidance of the imaging enabled by imaging assembly 10 (e.g. via ultrasound imaging and/or optical imaging such as OCT).

The microcatheter portion 1 can be exchanged out over a guidewire or advanced over another guidewire that is in the true lumen or various other permutations and the process of using distal portion of external sheath 1 interchangeably as a microcatheter or as the external sheath of an imaging catheter may continue.

In various example implementations, modifications may be made to a conventional intravascular imaging catheter or a conventional microcatheter as a result of the interchangeable use of the distal sheath portion 1 as either an imaging sheath or a microcatheter.

For example, unlike most microcatheters that have metal reinforcement up to near their distal end, the distal sheath portion 1 should be transmissive to the imaging energy that is used during imaging, for at least those sub-portions of the distal portion in which imaging is to take place. For example, it may be desirable to allow imaging only with the imaging assembly 10 is at its distalmost position within the main lumen. Alternatively, there may be a distal sub-portion, (e.g. a distal imaging window), such as a 10 cm long portion of the distal region of the distal sheath portion 1 that is transmissive to the imaging media to enable imaging during pullback. As such, the material forming the distal sheath portion 1 should be selected to permit this imaging.

In general, a high density of metal braiding precludes imaging with ultrasound or optical imaging. Typical materials with the desired properties for either optical or acoustic imaging include HDPE, LDPE, Pebax, Nylon, TPX and other polymer known in the art. The actual grade of polymer within each family can be selected based on the mechanical properties desired and the ability to mechanically couple the imaging window to other portions of the catheter (such as by thermal bonding, adhesives, crimping and other methods.

In various applications, it may be important or beneficial to position the imaging assembly 10 accurately within the distal region of the distal sheath portion 1. For example, it may be desirable to position the imaging assembly 10 to a distalmost location within the main lumen 11. However, this may be challenging to achieve when the imaging conduit includes a torque cable. A torque cable is typically hollow and may contain electrical wires or one or more fiber optics that transmit imaging signals between the imaging assembly 10 and proximal connector 8. The imaging conduit (e.g. a torque cable) may include one or more layers of wound metal filaments around a hollow lumen. The torque cable is preferably quite flexible, yet has reliable one-to-one transmission of torque between its proximal and distal ends. Torque cables may be quite compressible or extensible along their longitudinal axis, depending on how they are constructed.

One challenge with a torque cable that can stretch or compress along its long axis that relates to the present disclosure is that advancement of the torque cable within the distal sheath portion 1 may result in a suboptimal distance between the distal tip of the catheter and the imaging assembly. During advancement through the main lumen 11, the imaging conduit 17 would likely be longitudinally compressed due to friction between both the inner surface of the distal sheath portion 1 and the outer surfaces of the imaging assembly 10 and the imaging conduit 17. If the torque cable is then rotated, the imaging conduit 17 may or may not be relieved of some of that compression. In other words, if it is assumed that the imaging conduit is of fixed length, then the presence of friction and compression may cause the actual location of the imaging assembly within the distal sheath portion 1 to be proximal to the estimated position.

Furthermore, in some cases, the imaging assembly 10 may unintentionally extend out the distal port 14 of the intravascular imaging catheter, thus exposing the anatomy to rotating components and potentially inflicting trauma to the vessel and/or causing the device to fail. On other hand, if the imaging conduit is too short, the imaging assembly 10 will not be as distal as it otherwise could be.

In some example embodiments, an internal stop 60 may be provided at the distal end of the main lumen 11 of the distal sheath portion 1, as shown in FIGS. 4A, 4B, 4C, 4D and 4E.

Figure 4A:
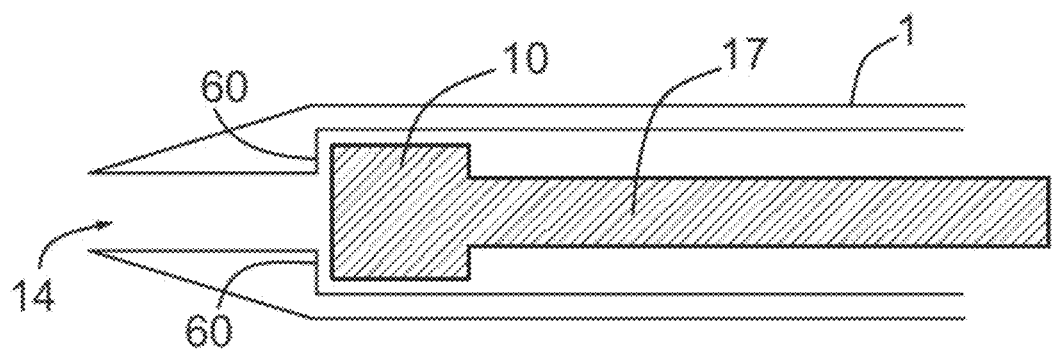
FIGS. 4A-F illustrate various example implementations of a structural stop for preventing the extension of the imaging assembly beyond a distal exit port while permitting the extension of the guidewire through the distal exit port.

FIG. 4A shows how imaging assembly 10 is advanced to the distal end of the main lumen and how stop 60, which is shown as completely circumferential, would prevent the imaging assembly 10 from exiting the distal sheath portion 1.

Figure 4B:
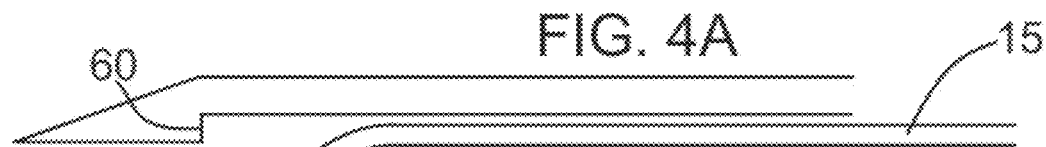

As shown in FIG. 4B, when the distal sheath portion 1 is used as a microcatheter and a guidewire 15 with a bend in its distal tip is advanced, the end of the tip 62 will likely be impeded by the stop 60.

Figure 4C:
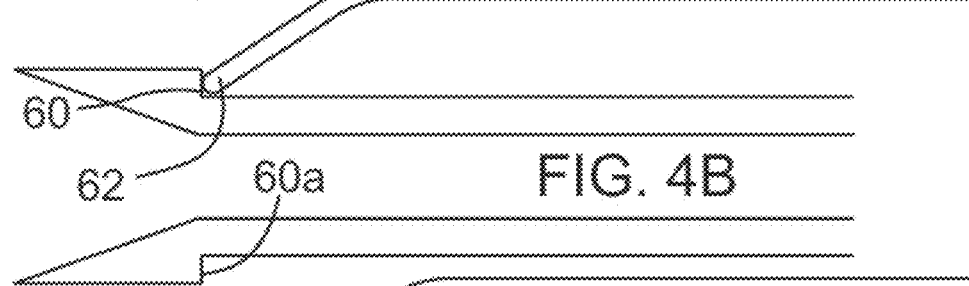
Figure 4D:
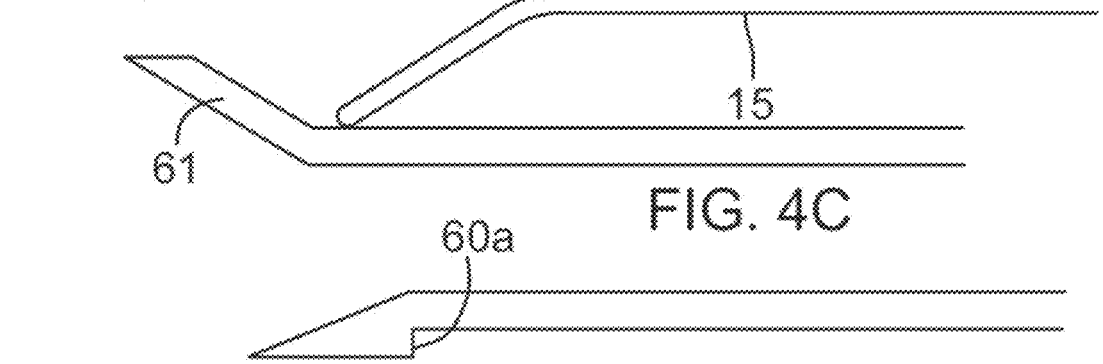
Figure 4E:
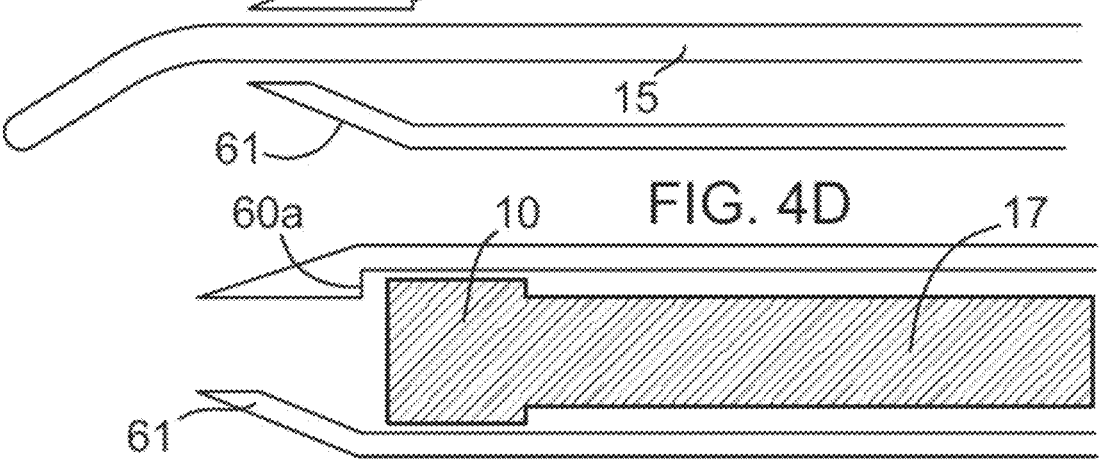

However, as shown in FIG. 4C, if stop 60a is not completely circumferential and the inner surface of the distalmost region of the distal sheath portion 1 has a more gradual tapered profile 61 over at least one portion of its inner surface, where the tapered region 61 (tapered inwardly towards the distal exit port) that is large enough to accept a guidewire 15 for passage through the distal exit port 14, then the guidewire 15 can extend out the distal end as shown in FIG. 4D. Meanwhile, the partial stop 60 will prevent the imaging assembly 10 from exiting via the distal exit port 14 as shown in FIG. 4E. Accordingly, in some example embodiments, the internal stop may be a partial stop that is configured to permit extension of a guidewire having a bent distal tip beyond the distal end of the distal elongate sheath. The partial stop may be configured such that the guidewire having the bent distal tip is extendable when the guidewire is rotated to one or more rotation angles relative to the partial stop, such that the guidewire does not encounter the internal stop during extension.

The partial stop may be provided as one or more protrusions that extend from an inner wall of the distal elongate sheath 1. The one or more protrusions may be configured (e.g. with suitable gaps thereamong or therebetween) to permit the extension of a guidewire while prohibiting extension of the imaging assembly 10. The protrusions may be configured to contact the imaging assembly without blocking a central axis of the distal elongate sheath.

In some example embodiments, the internal stop may be formed as an increased wall thickness of the distal elongate sheath, wherein the increased wall thickness produces an inwardly-directed step in the inner surface of the distal elongate sheath. The step may be sufficiently large to prevent passage of the imaging assembly beyond the distal end of the distal elongate sheath while permitting passage of the guidewire through the distal opening. The increased wall thickness may be defined over a fully circumferential region of the inner surface. Alternatively, the increased wall thickness may be defined over one or more portions of a circumferential region of the inner surface of the distal elongate sheath, such that the increased wall thickness forms a partial stop shaped as one or more partial annular segments, such as a half annulus.

It will be understood that although the distal region providing the stop and distal exit port is shown in FIGS. 4A-4E as being monolithically integrated with the distal sheath portion 1, this distal region may be provided by an additional component that is attached, affixed or otherwise connected to a distal end of the distal sheath portion 1.

Figure 4F:
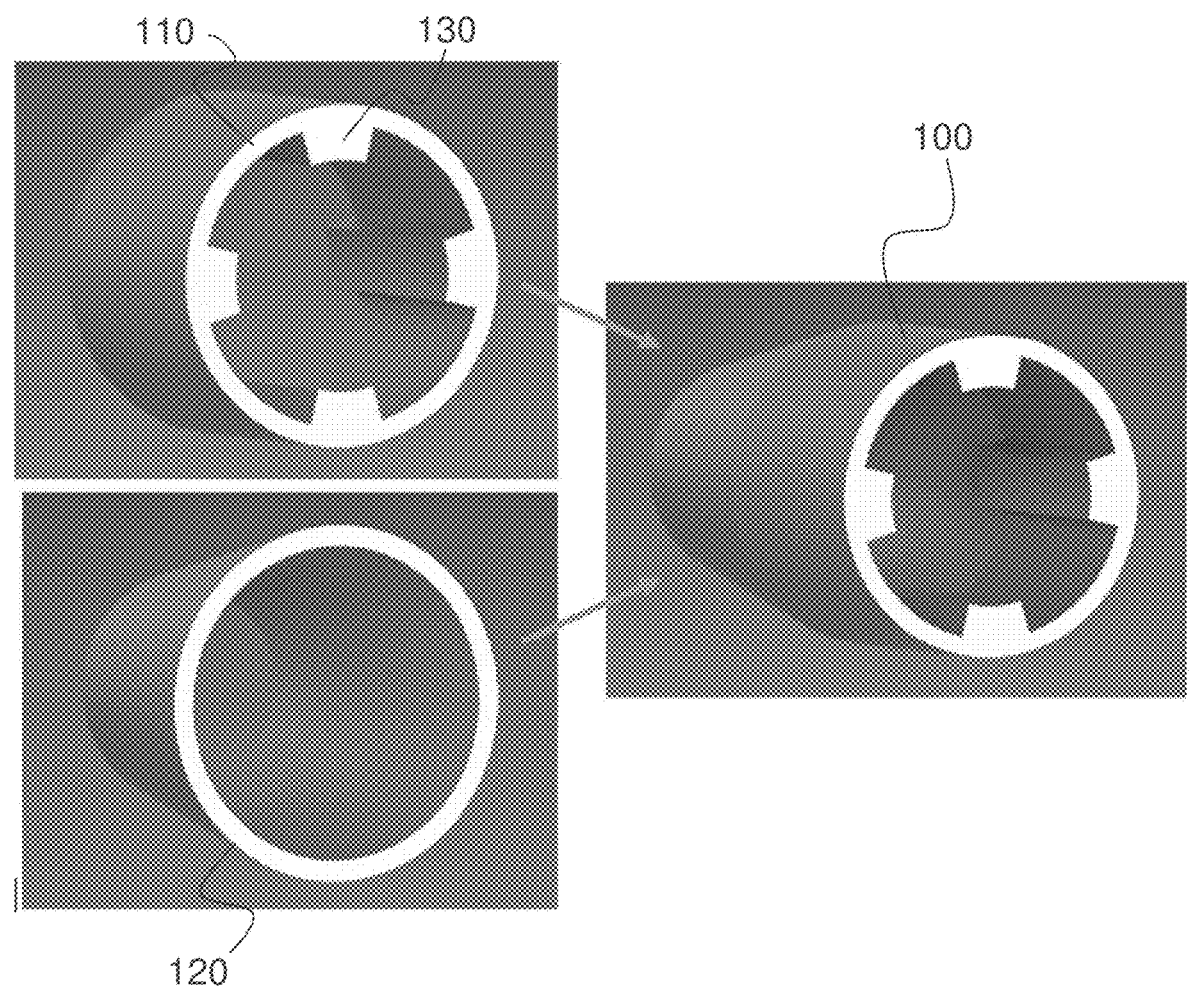

For example, as shown in FIG. 4F, the distal region of the distal sheath portion 1 may be provided as a distal cap 100 that is adhered to the remainder of the distal sheath portion 1. For example, a distal cap 100 may be adhered (e.g. attached, bonded) to the remainder of the distal sheath portion 1 using an adhesive or using a bonding method such as thermal bonding, ultrasonic welding and laser welding.

In one example implementation, the distal cap 100 may be integrally formed as a single component including an internal stop. As illustrated in FIG. 4F, the distal cap 100 may alternatively be formed as a multicomponent structure, including a distal portion 120 terminating in the distal opening, and a proximal portion 110 having or more internal stops formed therein, wherein the multiple components are adhered together to form the distal cap 100. In another example implementation, one or more stop structures for forming an internal stop within the distal cap 100 may be separately formed and adhered to an inner surface of the distal cap 100 prior to attachment of the distal cap 100 to the remainder of the distal sheath portion 1.

Figure 5A:
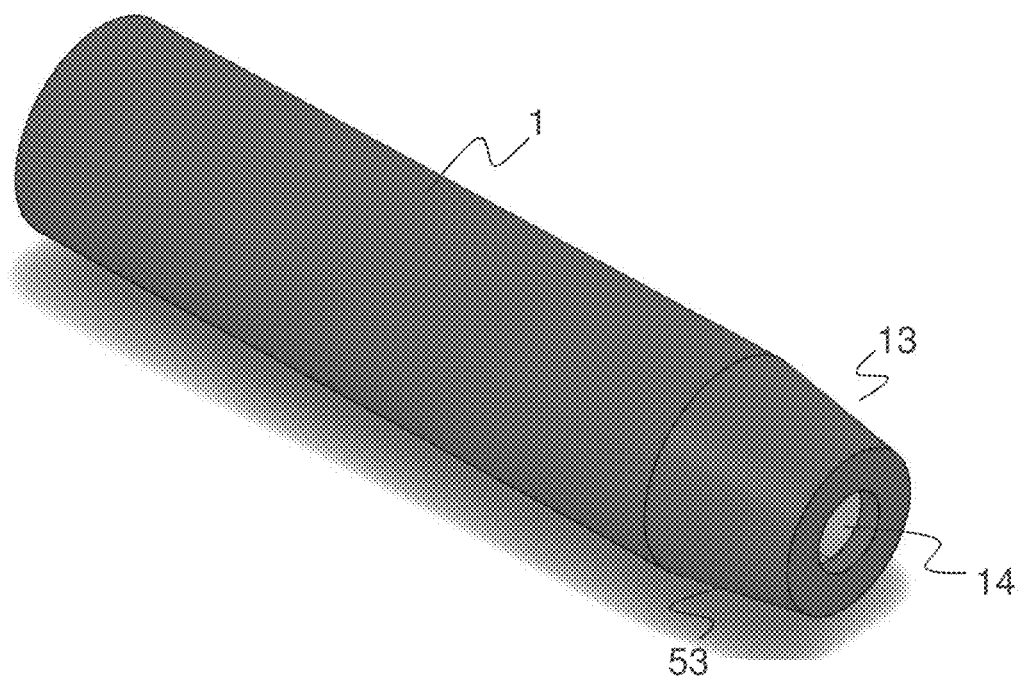
FIGS. 5A-B shows example views of an example distal sheath portion configured with a structural stop.

Referring now to FIG. 5A, an example implementation is shown in which the distalmost end of the distal sheath portion 1 is formed as tip 13 having a tapered profile (as shown at 53) on both its inner and outer surface. In the example implementation shown in the figure, the distalmost end is thus formed as a frustoconical shell.

Figure 5B:
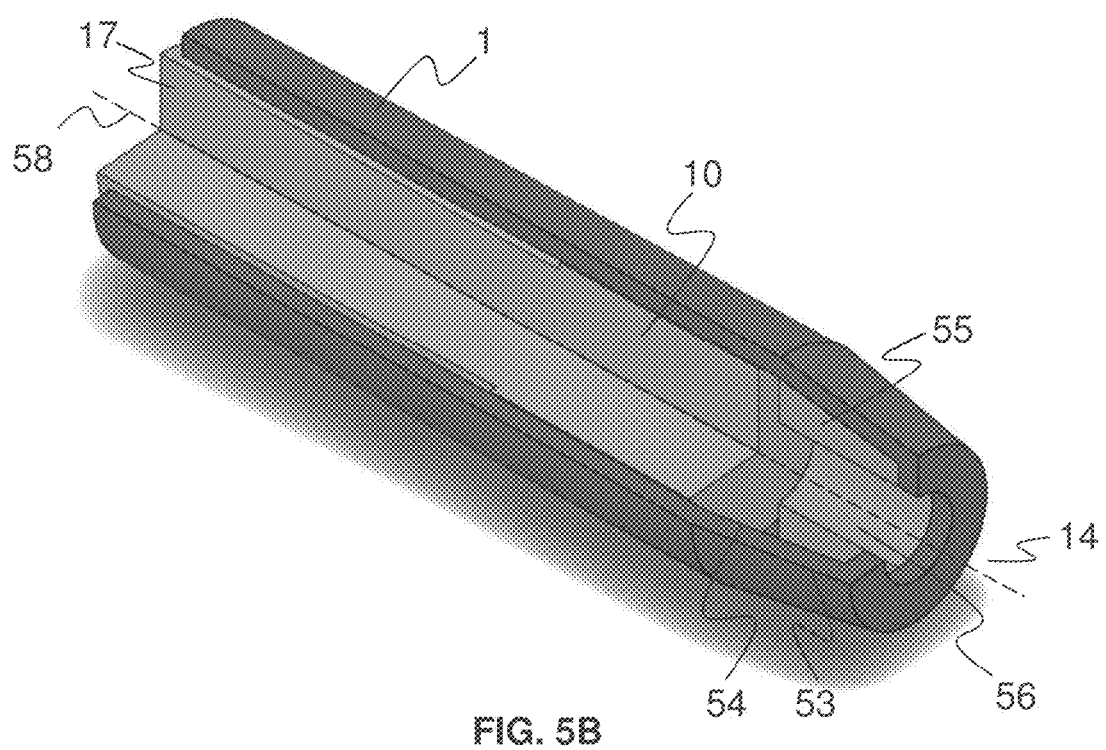

FIG. 5B shows a cut-away view of an example embodiment in which the distal region, having a tapered inner surface 54 and a tapered outer surface 53, includes an internal stop. In the non-limiting example illustrated in the figure, the internal stop is provided as a partial cone 55 (e.g. half a cone). In one example implementation, shown in the figure, the partial cone 55 may be formed with a hollow bore 56 extending through its center, which prevents the longitudinal extension of the imaging assembly 10 without blocking the central axis 58. The hollow bore may be provided with a radius that is sufficiently large to accept a guidewire therethrough (not shown in the figure). A partial cone structure having a hollow bore may be formed by first forming the cone with a hollow bore, and cutting (e.g. with a dicing saw) or otherwise modifying the cone (e.g. milling) along its long axis in order to produce a partial cone with the hollow bore. The partial cone may then be embedded into tip 13 of the catheter using techniques such as swaging.

Figure 6A:
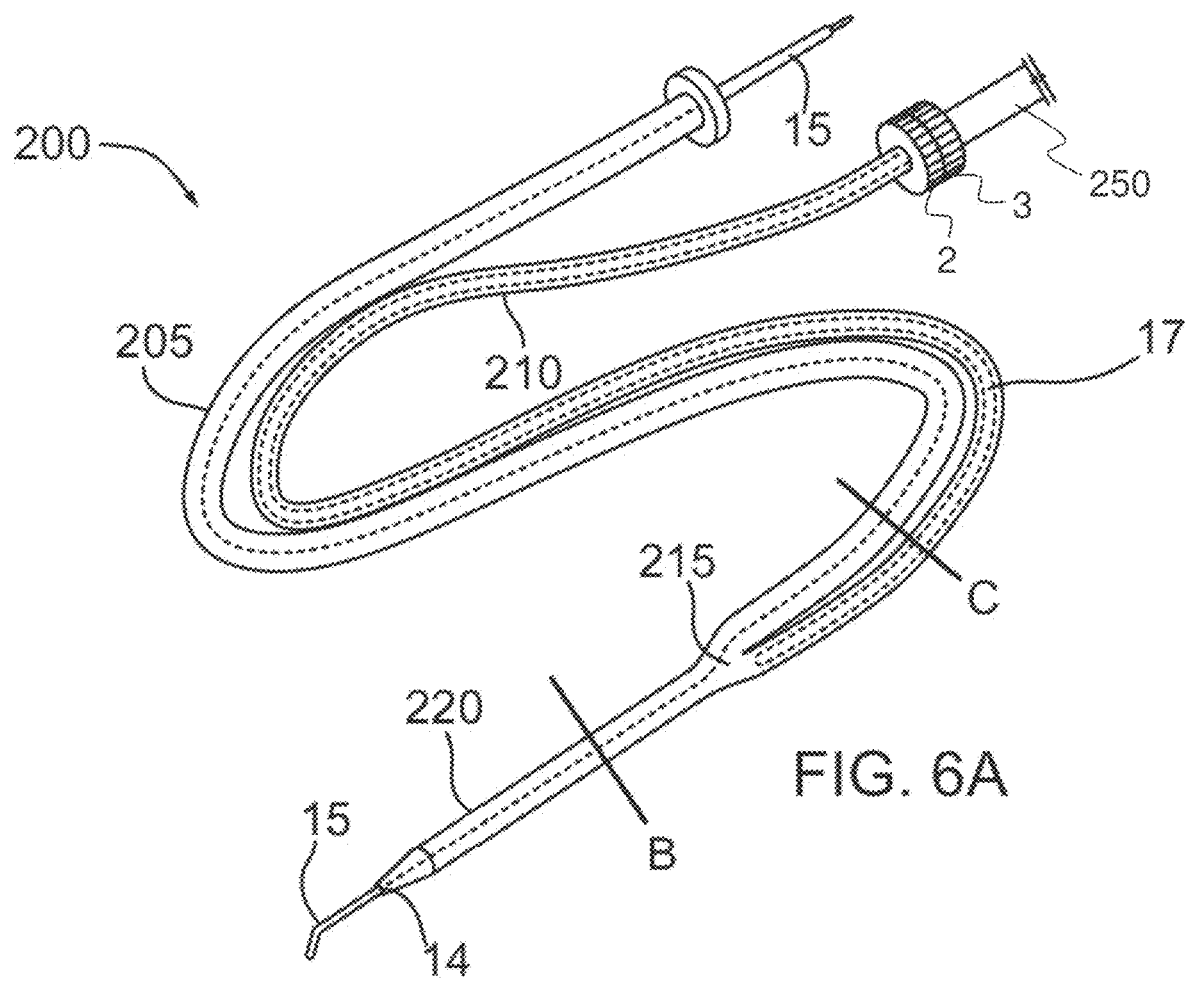
FIGS. 6A-C illustrate an alternative example of an intravascular imaging catheter having a bifurcated structure including first and second proximal sheath portions connected to a distal sheath portion.
Figure 6B:
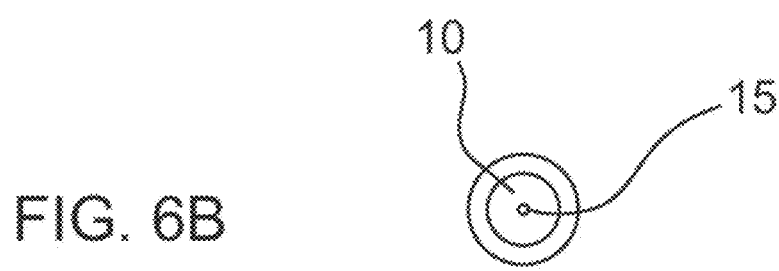
Figure 6C:
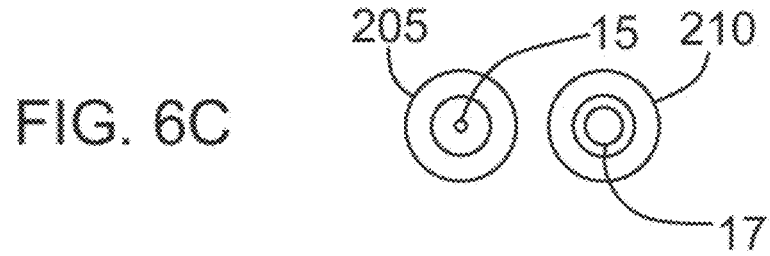

FIGS. 6A-C illustrate an alternative example embodiment of an intravascular imaging catheter 200 that includes a distal microcatheter portion that is configurable for guidewire placement and/or intravascular imaging. As shown in FIG. 6A, the example intravascular imaging catheter 200 includes a distal sheath portion 220 that may be configured to have dimensions suitable for use as a microcatheter when a guidewire is inserted therethrough.

Distal sheath portion 220 includes main lumen that may optionally house guidewire 15 or imaging conduit 17 (and imaging assembly 10). The figure shows the example case in which the guidewire 15 is extended into and through the distal sheath portion 220. Distal sheath portion 220 has a distal exit port 14 that is configured to permit the passage of guidewire 15. As described above, the distal end of the distal sheath portion 220 may be configured to prohibit (e.g. via a structural stop) the passage of the imaging assembly 10 when the imaging assembly 10 is translated, via the imaging conduit 17, to the distal end of the distal sheath portion 220.

As shown in FIG. 6A, the main lumen of distal sheath portion 220 is connected, via a bifurcation region 215, to respective lumens of a first proximal sheath portion 210 and a second proximal sheath portion 205. The second proximal sheath portion 205 is configured to house a guidewire 15, which can be optionally extended into, and retracted from, the distal sheath portion 220. The first proximal sheath portion 210 houses the imaging conduit 17 (having the imaging assembly 10 connected thereto at location remote from a proximal end thereof), where the imaging conduit 17 and associated imaging assembly 10 are optionally extendable into and retractable from the distal sheath portion 220 (using proximal pullback sheath portions, not shown). The first proximal sheath portion 210 may include a connector (not shown) that connects the intravascular imaging catheter to a patient interface module (alternatively called a motor drive unit). Alternatively, the first proximal sheath portion 210 may be connectable, via connectors 2 and 3, to an additional proximal sheath portion 250 that is detachable from the first proximal elongate sheath portion, thereby permitting withdrawal of a distal portion of the imaging conduit 17 from the first lumen of the first proximal sheath portion 210, and permitting the insertion of an additional elongate device into the first lumen and the extension of said additional elongate device into the third lumen. For example, the additional elongate device may include an additional guidewire, or a cable or conduit having a functional device (such as expandable balloon or an ablative device such as a laser ablation device) attached thereto a location that is remote from a proximal end thereof.

FIGS. 6B and 6C show cross-sectional views of the intravascular imaging catheter at two different longitudinal locations, where FIG. 6B shows a location along the distal sheath portion 220, and FIG. 6C shows a location proximal from the bifurcation region 215.

It will be understood that while FIG. 6A shows an example embodiment involving a proximal sheath portion for imaging and another proximal sheath portion for guidewire insertion, alternative example embodiments may include one or more additional proximal sheath portions. The one or more additional proximal sheath portions may be employed for the optional insertion of another guidewire (e.g. a guidewire of a different thickness or stiffness), an alternative imaging modality, or another non-imaging functional device, such as a therapeutic device.

In one example implementation, one or more of the proximal sheath portions shown in FIG. 6A may include two serially connectable sheath portions, which are removably connectable in manner shown in the example embodiment of FIG. 1 and FIGS. 2A-B, thereby allowing optional exchange of an internal guidewire, imaging conduit, or other functional device.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. An intravascular imaging catheter comprising:
a proximal elongate sheath comprising a first lumen;
a rotatable imaging conduit having a proximal portion housed within the first lumen and a distal portion extending beyond a distal end of said proximal elongate sheath;
an imaging assembly connected to said rotatable imaging conduit at a location that is remote from a proximal end of said rotatable imaging conduit, wherein a proximal end of said proximal elongate sheath is connectable to a motor drive unit for imparting rotation to said rotatable imaging conduit and said imaging assembly, and wherein said imaging assembly is configured for side viewing such that imaging energy is emitted and received at an angle relative to a longitudinal axis of said rotatable imaging conduit for collection of cross-sectional images as said imaging assembly is rotated; and
a distal elongate microcatheter sheath configured to be insertable within a vasculature of a subject, said distal elongate microcatheter sheath comprising a second lumen, wherein the second lumen is in fluid communication with a distal opening formed at a distal end of said distal elongate microcatheter sheath, said distal end of said proximal elongate sheath being connectable to a proximal end of said distal elongate microcatheter sheath;
wherein said intravascular imaging catheter resides in a disconnected state such that said proximal elongate sheath is disconnected from said distal elongate microcatheter sheath and such that said distal portion of said rotatable imaging conduit extends from said distal end of said proximal elongate sheath without residing within the second lumen of said distal elongate microcatheter sheath; and
wherein a distal region of said distal elongate microcatheter sheath comprises a partial internal stop configured such that when said distal portion of said rotatable imaging conduit is inserted into and extended within the second lumen of said distal elongate microcatheter sheath and said distal end of said proximal elongate sheath is connected to a proximal end of said distal elongate microcatheter sheath, said partial internal stop prevents passage of said imaging assembly beyond the distal end of the distal elongate microcatheter sheath, thereby protecting anatomy residing distal to the distal opening from rotating components of said intravascular imaging catheter and enabling extension of the imaging assembly to a location adjacent to said distal region for the collection of the cross-sectional images.

2. The intravascular imaging catheter according to claim 1 wherein said partial internal stop comprises one or more protrusions extending from an inner wall of said distal elongate microcatheter sheath into the second lumen, said one or more protrusions permitting passage of a guidewire therebetween, the guidewire having a distal bent portion.

3. The intravascular imaging catheter according to claim 1 wherein said partial internal stop comprises an increased wall thickness of said distal elongate microcatheter sheath, said increased wall thickness producing an inwardly-directed step in an inner surface of said distal elongate microcatheter sheath such that passage of said imaging assembly beyond said inwardly-directed step is prevented.

4. The intravascular imaging catheter according to claim 3 wherein said increased wall thickness forms said partial internal stop shaped as one or more partial annular segments.

5. The intravascular imaging catheter according to claim 4 wherein said inwardly-directed step is shaped as a half-annulus.

6. The intravascular imaging catheter according to claim 3 wherein said inwardly-directed step is provided over a first circumferential region of said distal elongate microcatheter sheath, and wherein a second circumferential region of said distal elongate microcatheter sheath is absent of said inwardly-directed step, and wherein a radius of said inner surface, within said first circumferential region, is constant between said inwardly-directed step and said distal end of said distal elongate microcatheter sheath.

7. The intravascular imaging catheter according to claim 6 wherein said distal elongate microcatheter sheath is inwardly tapered, within said second circumferential region, over a tapered region extending from said partial internal stop toward said distal end of said distal elongate microcatheter sheath.

8. The intravascular imaging catheter according to claim 1 wherein said partial internal stop does not block a central axis of said distal elongate microcatheter sheath.

9. The intravascular imaging catheter according to claim 1 wherein said distal elongate microcatheter sheath comprises a primary elongate sheath portion and a distal cap adhered thereto.

10. The intravascular imaging catheter according to claim 1 wherein said distal elongate microcatheter sheath comprises a primary elongate sheath portion and a distal cap adhered thereto, wherein said distal cap comprises said partial internal stop.

11. The intravascular imaging catheter according to claim 10 wherein said partial internal stop is integrally formed with said distal cap.

12. The intravascular imaging catheter according to claim 10 wherein said partial internal stop is adhered within said distal cap.

13. The intravascular imaging catheter according to claim 1 wherein said proximal elongate sheath comprises a first sheath portion and a second sheath portion, wherein said first sheath portion is translatable relative to said second sheath portion for varying a longitudinal position of said imaging assembly.

14. The intravascular imaging catheter according to claim 1 wherein said distal elongate microcatheter sheath comprises a single central lumen.

15. The intravascular imaging catheter according to claim 1 wherein said distal region comprises a transparent window that is transparent to imaging energy emitted and/or received by said imaging assembly.

16. The intravascular imaging catheter according to claim 1 wherein at least a portion of said distal region is formed from a material that is transparent to imaging energy emitted and/or received by said imaging assembly.

17. The intravascular imaging catheter according to claim 1 wherein an outer diameter of said distal elongate microcatheter sheath is less than 4 French.

18. The intravascular imaging catheter according to claim 1 wherein said partial internal stop comprises a proximal-facing contact surface configured to contact said imaging assembly and prevent said passage of said imaging assembly beyond the distal end of the distal elongate microcatheter sheath, said partial internal stop being absent of a distal-facing contact surface parallel to the proximal-facing contact surface, and wherein said distal elongate microcatheter sheath is inwardly tapered over a tapered region extending from said partial internal stop toward said distal end of said distal elongate microcatheter sheath.

* * * * *